US010206806B2

(12) United States Patent
Brown

(10) Patent No.: US 10,206,806 B2
(45) Date of Patent: Feb. 19, 2019

(54) MULTI-VECTOR TRACTION DEVICE FOR THE LUMBAR SPINE

(71) Applicant: Matthew James Brown, Dallas, TX (US)

(72) Inventor: Matthew James Brown, Dallas, TX (US)

(*) Notice: Subject to any disclaimer, the term of this patent is extended or adjusted under 35 U.S.C. 154(b) by 431 days.

(21) Appl. No.: 14/659,256

(22) Filed: Mar. 16, 2015

(65) Prior Publication Data

US 2015/0257916 A1 Sep. 17, 2015

Related U.S. Application Data

(60) Provisional application No. 61/954,475, filed on Mar. 17, 2014, provisional application No. 62/046,054, filed on Sep. 4, 2014.

(51) Int. Cl.
*A61F 5/00* (2006.01)
*A61F 5/042* (2006.01)

(52) U.S. Cl.
CPC .................................. *A61F 5/042* (2013.01)

(58) Field of Classification Search
CPC ...... A61H 1/0296; A61H 1/0292; A61H 1/02; A61H 1/0222; A61H 1/0229; A61H 1/0218; A61H 2201/1621; A61H 2201/1626; A61G 13/00–13/08; A63B 22/0087; A63B 21/4029–21/4031; A63B 23/0238; A63B 21/00185; A63B 21/151
USPC ................ 602/36, 32, 33, 34, 35, 40; 5/601
See application file for complete search history.

(56) References Cited

U.S. PATENT DOCUMENTS

| 2,475,003 A | * | 7/1949 | Black | A61G 13/009 5/613 |
| 2,865,367 A | * | 12/1958 | Sorenson | A61H 1/0222 606/243 |
| 3,005,633 A | * | 10/1961 | Riemer | A61G 13/009 297/300.1 |
| 3,167,789 A | * | 2/1965 | Wicks | A61G 7/103 5/81.1 HS |
| 3,420,229 A | * | 1/1969 | Miller | A61H 1/0222 606/243 |
| 3,428,307 A | * | 2/1969 | Kennedy | A47B 1/02 108/138 |
| 3,654,921 A | * | 4/1972 | Neuhardt, Jr. | A61H 1/0218 602/33 |

(Continued)

*Primary Examiner* — Keri J Nelson
*Assistant Examiner* — Adam Baker
(74) *Attorney, Agent, or Firm* — Rachel L. Carnaggio; Holland & Hart LLP

(57) ABSTRACT

Some embodiments of the present disclosure include a traction device for relieving lower back pain and stiffness and reducing lumbar spine intervertebral disc displacement. The device may include a sliding spine assembly attached to a head rest pad, a torso pad, and a hip pad, an adjustable length vector bar extending outwardly from the spine assembly, wherein the vector bar is rotatably attached to the sliding spine assembly such that the vector bar is configured to move in a plurality of vectors, a cross bar foot brace tube attached to the vector bar; a foot rest positioned on the foot brace tube, a belt positioned proximate to the torso pad, and a strap assembly attached to the foot brace tube or the distal end of the vector bar, the strap assembly configured to attach to the belt and apply traction to a user's back.

20 Claims, 5 Drawing Sheets

(56) References Cited

U.S. PATENT DOCUMENTS

| | | | | |
|---|---|---|---|---|
| 3,741,200 | A * | 6/1973 | Morin | A61H 1/0222 606/243 |
| 3,986,499 | A * | 10/1976 | Fischer | A61H 1/0292 606/242 |
| 4,580,554 | A * | 4/1986 | Goodley | A61H 1/0229 606/201 |
| 4,641,637 | A * | 2/1987 | Rosen | A61H 1/0218 602/35 |
| 4,865,022 | A * | 9/1989 | Gorsen | A61H 1/0218 602/33 |
| 5,820,520 | A * | 10/1998 | Sieber | A63B 23/0227 482/148 |
| 6,533,744 | B1 * | 3/2003 | Stanish | A61F 5/04 602/33 |
| 7,033,333 | B1 * | 4/2006 | Croft | A61F 5/04 602/17 |
| 7,083,556 | B1 * | 8/2006 | Miskech | A61H 1/0292 482/140 |
| 7,104,935 | B2 * | 9/2006 | Matsuoka | A63B 21/0004 482/121 |
| 7,762,936 | B2 * | 7/2010 | Conley | A61H 1/0244 482/131 |
| 8,257,285 | B2 * | 9/2012 | Cook | A61H 1/005 5/915 |
| 2003/0139266 | A1 * | 7/2003 | Lin | A61H 1/001 482/140 |
| 2007/0287946 | A1 * | 12/2007 | Kendrick | A61F 5/04 602/36 |
| 2014/0087929 | A1 * | 3/2014 | Sussman | A63B 21/1465 482/139 |

* cited by examiner

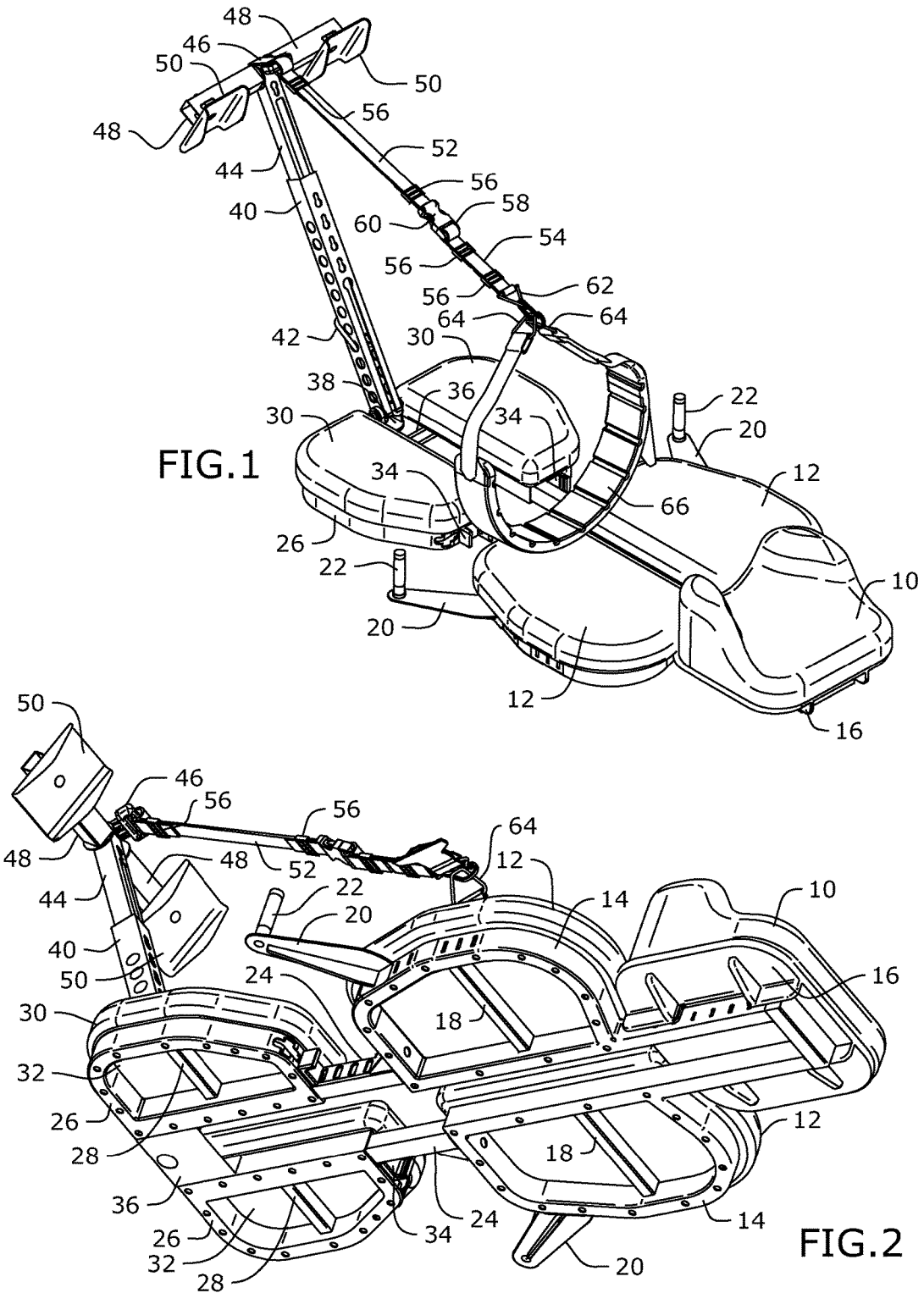

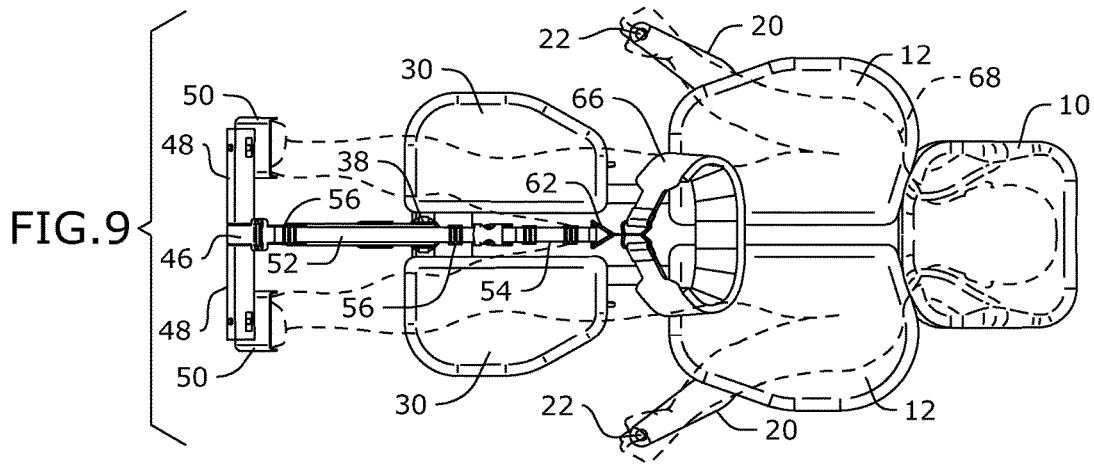
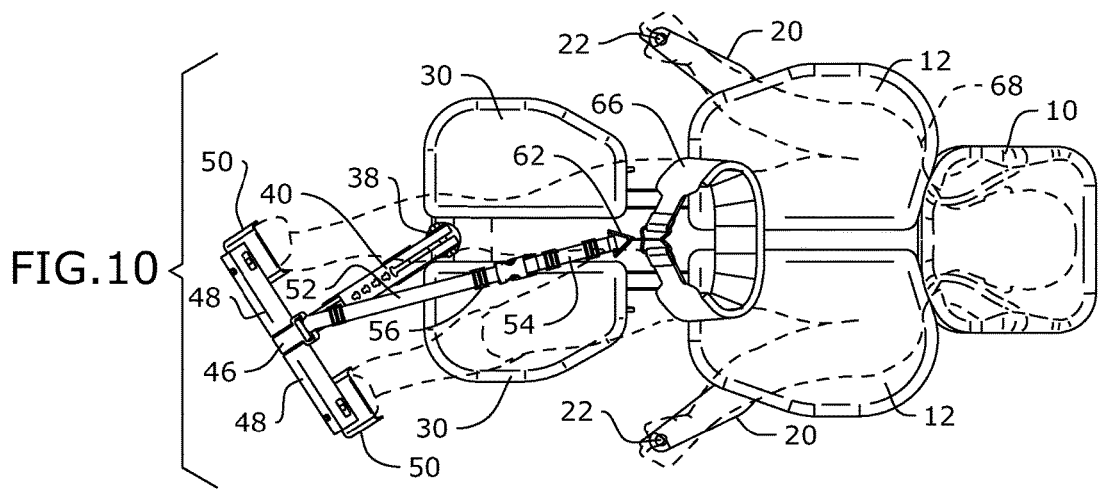
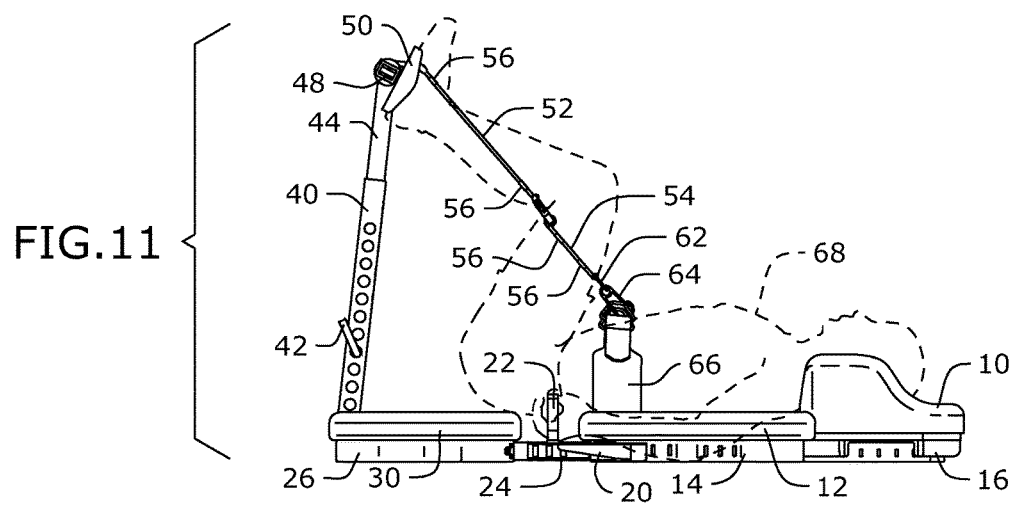

MULTI-VECTOR TRACTION DEVICE FOR THE LUMBAR SPINE

RELATED APPLICATIONS

This application claims priority to provisional patent applications U.S. Ser. No. 61/954,475 filed on Mar. 17, 2014 and U.S. Ser. No. 62/046,054 filed on Sep. 4, 2014, the entire contents of each of which is herein incorporated by reference.

BACKGROUND

The embodiments herein relate generally to back pain relief, and more particularly, to a device providing for the application of multi-vector, auto-powered traction by a user to his or her lumbar spine.

Lower back pain is a leading cause of work disability and lost productivity. Treatments are complex and costly. Most lumbar spine conditions require repetitive, ongoing physical training and decompression. Conventional devices designed to provide such physical training and decompression only provide pure longitudinal fraction along a flat plane and anchor under the arms and ankles, which limits the direction of force to only a single plane of traction. However, lumbar spine disc and facet join lesions are typically asymmetrical and varied in their presentation. A single plane of traction can only provide traction in one direction and cannot be tailored to the many variables presented by the user. Moreover, these devices also are not comfortable for the user. Motorized systems are set to apply force at a pre-determined setting, which is not based on the comfort of the user.

Therefore, what is needed is a multi-vector, auto-powered device configured to provide traction, stretching, and decompression forces to the lumbar spine.

SUMMARY

Some embodiments of the present disclosure include a traction device for relieving lower back pain and stiffness and reducing lumbar spine intervertebral disc displacement. The device may include a sliding spine assembly attached to a head rest pad, a torso pad, and a hip pad, an adjustable length vector bar extending outwardly from the spine assembly, wherein the vector bar is rotatably attached to the sliding spine assembly such that the vector bar is configured to move in a plurality of vectors, a cross bar foot brace tube attached to the vector bar; a foot rest positioned on the foot brace tube, a belt positioned proximate to the torso pad, and a strap assembly attached to the foot brace tube or the distal end of the vector bar, the strap assembly configured to attach to the belt and apply traction to a user's back.

BRIEF DESCRIPTION OF THE FIGURES

The detailed description of some embodiments of the invention is made below with reference to the accompanying figures, wherein like numerals represent corresponding parts of the figures.

FIG. 1 is a top perspective view of one embodiment of the present invention.

FIG. 2 is a bottom perspective view of one embodiment of the present invention.

FIG. 9 is a top view of one embodiment of the present invention, shown in use and demonstrating a straight vector.

FIG. 10 is a top view of one embodiment of the present invention, shown in use and demonstrating a left vector.

FIG. 11 is a side view of one embodiment of the present invention.

DETAILED DESCRIPTION OF CERTAIN EMBODIMENTS

Figure 3:
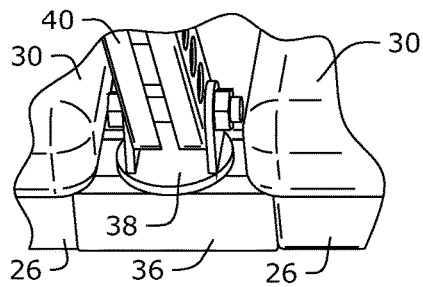
FIG. 3 is a detail perspective view of one embodiment of the present invention.
Figure 5:
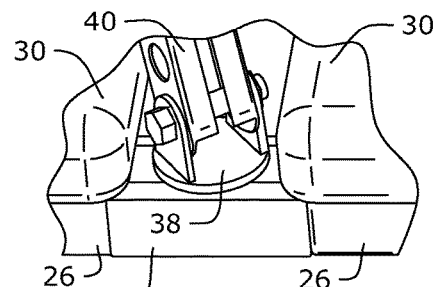
FIG. 5 is a detail perspective view of one embodiment of the present invention.
Figure 4:
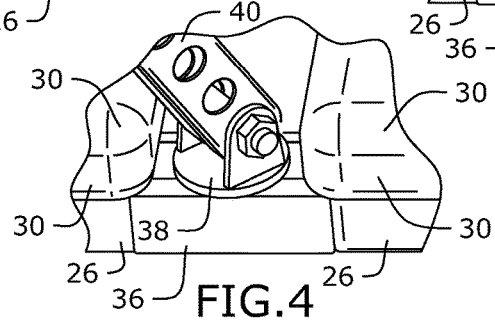
FIG. 4 is a detail perspective view of one embodiment of the present invention.
Figure 6:
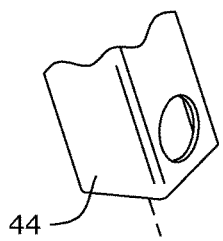
FIG. 6 is an exploded detail view of one embodiment of the present invention.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to relieve lower back pain, reduce lumbar spine intervertebral disc displacement, and relieve lower back stiffness and may comprise the following elements: (i) Torso Board, Hip Board, and Head Rest; (ii) Adjustable Vector Bar; (iii) Belt; and (iv) Strap Assembly. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

The various elements of the traction device of the present disclosure may be related in the following exemplary fashion. It is not intended to limit the scope or nature of the relationships between the various elements and the following examples are presented as illustrative examples only.

By way of example, and referring to FIGS. 1-14, some embodiments of the traction device for relieving lower back pain and stiffness and reducing lumbar spine intervertebral disc displacement of the present disclosure comprise a sliding spine assembly 24; a head rest pad 10, a torso pad 12, and a hip pad 30 attached to the spine assembly 20, the head rest pad 10 being attached to a first end of the spine assembly 20, the hip pad 30 being attached proximate to a second end of the spine assembly 20, and the torso pad 12 being positioned between the head rest pad 10 and the hip pad 30; an adjustable length vector bar extending outwardly from the second end of the spine assembly 24, wherein the adjustable length vector bar may comprise a substantially hollow split rectangular tube 40 configured to accept and engage with a leg press tube 40, wherein the leg press tube 40 may be locked in a desired position using a locking mechanism, such as a yoke lock 42 and may comprise a foot end cap 46 positioned at an end thereof, and wherein the vector bar may be rotatably attached to the spine assembly 20, such as by using an articulating joint 38 configured to engage with an articulating joint base 36 on the sliding spine assembly 20; a cross bar foot brace tube 48 attached to an end of the vector bar distal from the spine assembly 20; a pair of foot rests 50 positioned on foot brace tube 48; belt 66 attached to, or positioned proximate to, the torso pad 12; and a strap assembly attached to the foot brace tube 48 or to the distal end of the vector bar, the strap assembly configured to attach to the belt 66, wherein when a user 68 is positioned on the traction device, the belt 66 is configured to encircle the user 28, the user's feet are positioned against the foot rests 50, and the strap assembly is configured to apply traction to the belt 66, which may be aligned with the user's lumbar spine. The user 68 may alter the traction provided to the belt 66 by moving the vector bar to multiple vectors from the user's midline, as shown in FIGS. 9-13. Alternatively, in other embodiments, the vector bar may remain substantially stationary and the user may vary the traction provided to the belt 66 by sliding the torso pad 12 along the sliding spine assembly 24, in a fashion similar to a rowing machine. In some embodiments, the traction device may further comprise a pair of handles 22 extending outwardly from a handle bracket 20, which may be attached to the torso pad 12, providing the user 68 with handles to help with stability and positioning during use of the device. Thus, embodiments of the device may not require a motor or other electronic components to be used properly.

In embodiments, the head rest pad 10 may be supported by a head rest frame comprising a head rest bracket 16, as shown in FIGS. 1 and 2. The head rest bracket 16 may be attached to the first end of the sliding spine assembly 24. In some embodiments, the head rest pad 10 may be contoured to comfortably accommodate a user's head.

In embodiments, the torso pad 12 may be supported by a torso pad frame attached to the sliding spine assembly 24, the torso pad frame comprising a pair of curved torso tubes 14 attached proximate to outer edges of the bottom surface of the torso pad 12, defining an interior region of the torso pad 12, and a torso support tube 18 configured to bisect the interior region, as shown in FIG. 2. The torso pad 12 may be attached to the sliding spine assembly 24, such that the torso pad 12 remains stationary while the traction device is in use, as shown in FIGS. 1-13.

Figure 7:
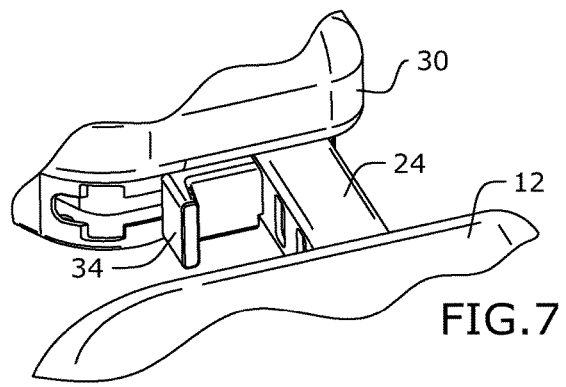
FIG. 7 is a perspective detail view of one embodiment of the present invention, shown in an exemplary initial state.
Figure 8:
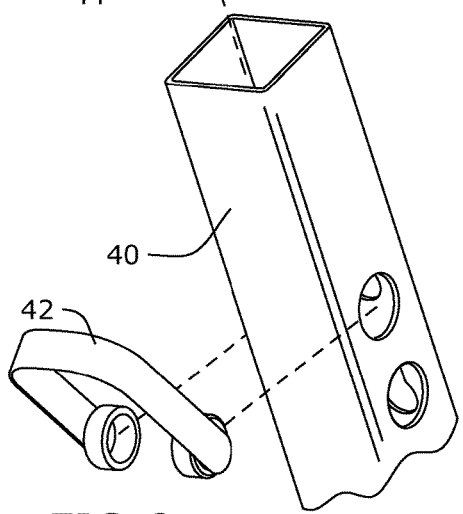
FIG. 8 is a perspective detail view of one embodiment of the present invention, shown in an exemplary secondary state.
Figure 12:
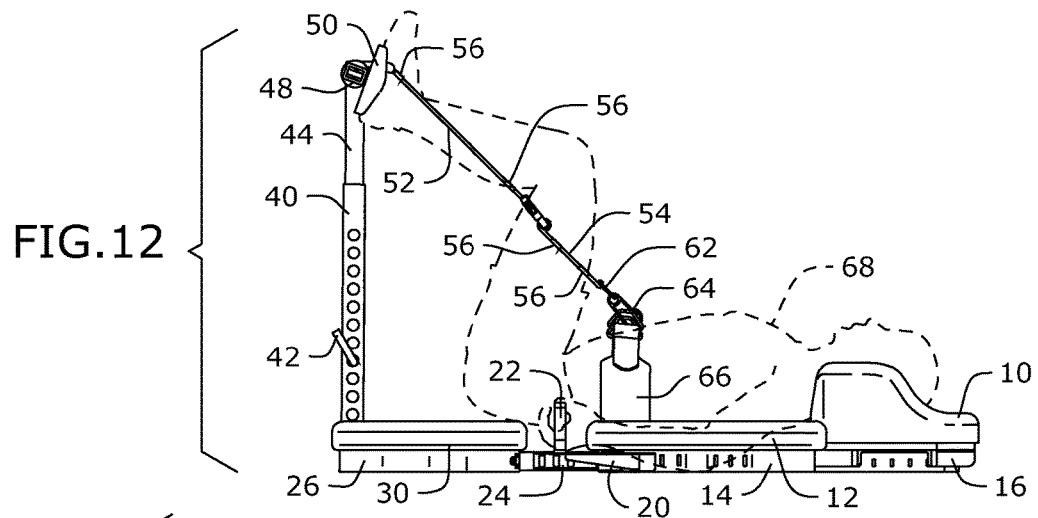
FIG. 12 is a side view of one embodiment of the present invention, demonstrating a partial press.
Figure 13:
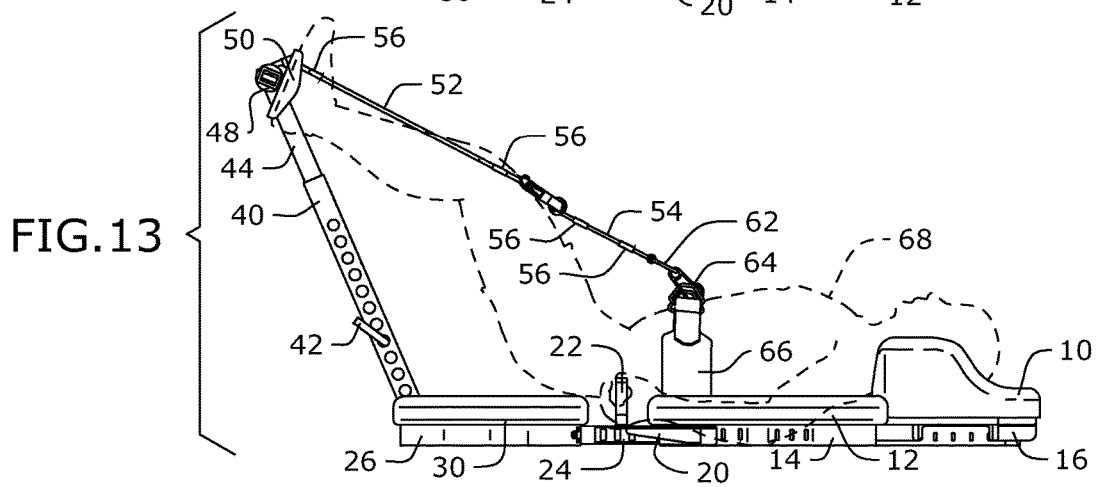
FIG. 13 is a side view of one embodiment of the present invention, demonstrating a full leg extension press.

In embodiments, the hip pad 30 may be supported by a hip pad frame attached proximate to the second end of the sliding spine assembly 24, the hip pad frame comprising a hip board 32 onto with the hip pad 30 is adhered or otherwise attached, a pair of curved hip tubes 26 attached proximate to the outer edges of the bottom surface of the hip board 32, defining an interior region of the bottom surface of the hip board 32, and a hip support tube 28 configured to bisect the interior region, as shown in FIG. 2. The curved hip tubes 26 may each comprise a substantially straight portion, wherein the substantially straight portion may be configured to accommodate a length of the sliding spine assembly 24, such that the sliding spine assembly 24 may telescopically extend outwardly from the curved hip tubes 26. As shown in FIGS. 7 and 8, the hip pad 30 may comprise a locking mechanism to locking the sliding spine assembly 24 into its desired configuration. As shown in the Figures, the locking mechanism may comprise a hip lock 34 configured to engage with locking orifices in the sliding spine assembly 24.

As described above, the strap assembly may be attached to the foot brace tube 48 or to the distal end of the vector bar, wherein the strap assembly is configured to attach to the belt 66. For example, as shown in FIGS. 1, 2, and 9-13, the strap assembly may comprise a first strap 54 attached to the belt 66 and a second strap 52 attached to the leg press tube 44, wherein the first strap 54 and the second strap 52 are configured to removably attach to one another using a fastener, such as a buckle having a female portion 58 and a male portion 60. The straps 52, 54 may also comprise a plurality of clips 56 that allow a user 68 to adjust the length of each strap 52, 54. As shown in the Figures, the first strap 54 may comprise a ring, such as an angular carabineer 62, positioned at an end of the first strap 54 distal from the foot brace tube 48, wherein the angular carabineer 62 may be removably attached to a pair of belt rings 64 on the belt, wherein when the angular carabineer 62 is attached to the belt rings 64, the belt 66 may be secured around a user's waist. The straps 52, 54 may be made of any desirable material and, in some embodiments, comprise an elastic material.

As described above, the belt 66 may comprise a mechanism, such as belt rings 64, for attaching to the first strap 54. The belt rings 64 may be positioned at opposite ends of the belt 66, as shown in the Figures. The belt 66 may be made of any suitable or desired material and, in some embodiments, comprises curved foam.

Both the sliding spine assembly 24 and the vector bar may be adjustable in length to accommodate users of different sizes. For example, the sliding spine assembly 24 and the vector bar may each telescope to achieve the necessary length, wherein the sliding spine assembly 24 and the vector bar may be secured in the desired position using a locking mechanism, such as a yoke lock 42 or a hip lock 34, wherein the locking mechanism may be configured to engage with locking orifices on the sliding spine assembly 24 and the vector bar, respectively. The vector bar may comprise a range of motion resulting from its ability to pivot at the connection point between the vector bar and the sliding spine assembly 24 due to, for example, the articulating joint 38 assembly. The range of motion may comprise multiple vectors relative to a user's midline or to the joint between the vector bar and the sliding spine assembly.

In embodiments, the traction device may optionally include a digital/mechanical force meter/scale to measure to number of pounds of force being applied, wherein the meter/scale may be attached to the device at any location viewable by the user. An optional counter-lever bar could articulate to the base of the vector bar to provide cephalad traction to the upper torso, thoracic spine, and/or cervical spine/occiput/cranium.

Figure 14:
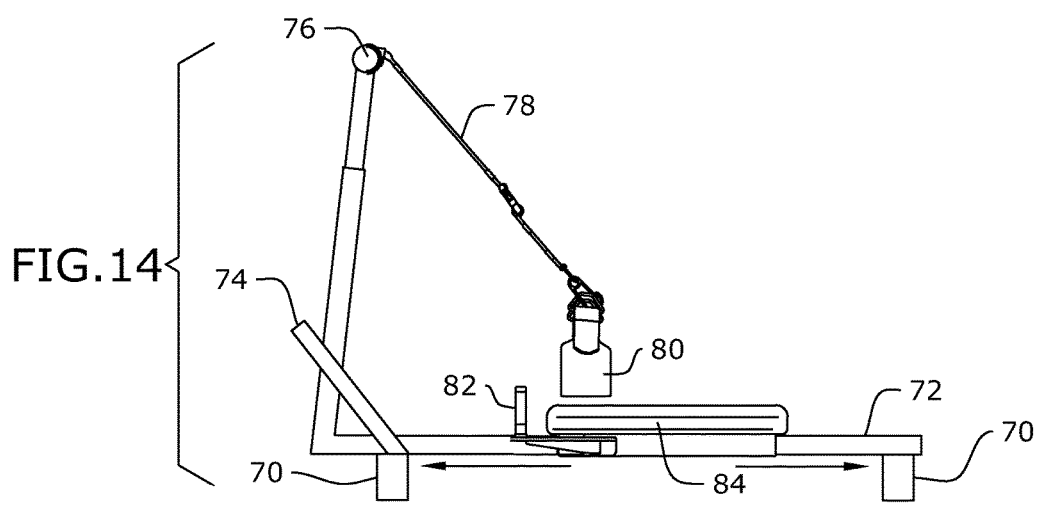
FIG. 14 is a side view of one embodiment of the present invention.

As shown in FIG. 14, alternate embodiments may comprise a pad that glides along a frame of the traction device, rather than a device that includes stationary pads, as shown in FIGS. 1-13. For example, the traction device may comprise a gliding seat 84, optionally including a pair of grip handles 82, configured to glide along a gliding track base 72, which may be supported by support legs 70, which may lift the device slightly off of the ground. A foot rest 74 may extend upwardly from the gliding track base 72 at an angle. A support bar 76, which may be similar to the rectangular tube 40, but which is stationary rather than moveable, may extend upward from the gliding track base 72, wherein the strap assembly 78 may extend from an end of the support bar 76 distal from the gliding track base 72. The strap assembly 78 may attach to a belt 80, which may be configured to wrap around a user's waist. To use the alternate embodiment, a user may lie on the gliding seat 84 with the belt 80 around his or her waist and push on the foot rest 74, causing the gliding seat 84 to glide along the length of the gliding track base 72.

Each component of the device may have any desired shape and size and may be connected to other components using any conventional fasteners. Because of the design of the device, the device may be portable and user friendly, and may not require a motor, but rather may be powered by muscle resistances from the user, applying a traction force to the lumbar spine in multiple planes.

To use the traction device, a user 68 may lay on the device, placing hips on the hip pad 30, torso on the torso pad 12, and head on the head rest pad 10. The user 68 may attach the belt 66 around the waist, attach the strap assembly to the belt 66, grip the handles 22, and place the feet on the foot rests 50. By extending the legs, the user may press on the foot rests 50, causing the strap assembly to apply traction to the belt 66 and, thus, to the user's back. Depending on the desired outcome of using the device, the user 68 may alter the traction provided to the belt 66 by moving the vector bar to various vectors from the user's midline, wherein the vector bar is configured to move to any desired vector, as shown in FIGS. 9 and 10.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

Figure 15:
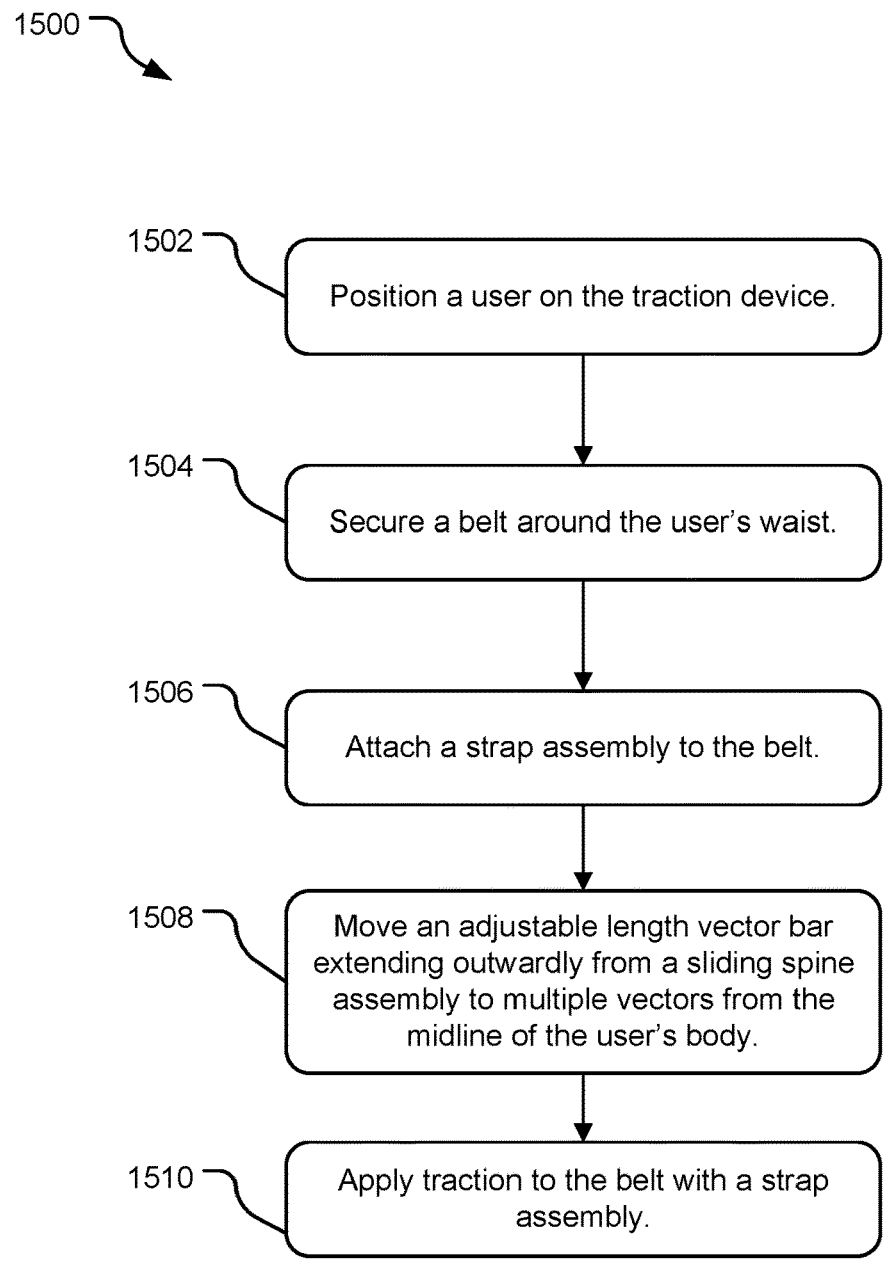
FIG. 15 is a flowchart of example operations for using a traction device.

FIG. 15 is a flowchart of example operations 1500 for using a traction device. An operation 1502 positions a user on the traction device. An operation 1504 securing a belt around the user's waist. An operation 1506 attaches a strap assembly to the belt. An operation 1508 moves an adjustable length vector bar extending outwardly from a sliding spine assembly to multiple vectors from the midline of a user's body. An operation 1510 applies traction to the belt with the strap assembly.

What is claimed is:

1. A traction device for relieving lower back discomfort pain and stiffness and reducing lumbar spine intervertebral disc displacement, the device comprising:
    a sliding spine assembly;
    an adjustable length, pivotable vector bar extending outwardly from a first end of the sliding spine assembly, wherein the adjustable length, pivotable vector bar is rotatably attached to the sliding spine assembly;
    an articulating joint located on a first end of the adjustable length, pivotable vector bar configured to engage with an articulating joint base attached to the sliding spine assembly to rotate the adjustable length, pivotable vector bar about more than one axis of rotation;
    a cross bar foot brace tube attached to a second end of the adjustable length, pivotable vector bar distal from the sliding spine assembly;
    a foot rest positioned on the cross bar foot brace tube;
    a belt configured to encircle a user in alignment with the user's lumbar spine; and
    a strap assembly configured to attach to the belt and to the foot rest, wherein when the user is positioned on the traction device, the user's feet are positioned against the foot rest and the strap assembly is configured to apply traction to the belt when the user pushes on the foot rest, wherein pushing on the foot rest moves the adjustable length, pivotable vector bar and the strap assembly in more than one axis of rotation, thereby applying traction to the user's back.

2. The traction device of claim 1, wherein the adjustable length vector bar comprises a substantially hollow split rectangular tube configured to accept and engage with a leg press tube, wherein the leg press tube is locked in a desired position using a lock.

3. The traction device of claim 2, wherein the lock is a yoke lock.

4. The traction device of claim 1, wherein the strap assembly comprises:
    a first strap attached to the belt; and
    a second strap attached to a member selected from a group comprising of the foot brace tube and the distal end of the adjustable length, pivotable vector bar, wherein the first strap and the second strap are configured to removably attach to one another using a fastener and a length of each strap is adjustable.

5. The traction device of claim 4, wherein
    the first strap comprises an angular carabiner positioned at an end of the first strap distal from the second strap;
    the angular carabiner is configured to removably attach to a pair of belt rings attached to the belt; and
    when the angular carabiner is attached to the belt rings, the belt is secured around the user's waist.

6. The traction device of claim 1, further comprising:
    a head rest pad, a torso pad, and a hip pad attached to the sliding spine assembly, the head rest pad being attached to a first end of the sliding spine assembly, the hip pad being attached proximate to a second end of the sliding spine assembly, and the torso pad being positioned between the head rest pad and the hip pad and proximate to the belt.

7. The traction device of claim 6, wherein the torso pad is supported by a torso pad frame attached to the sliding spine assembly, the torso pad frame comprising:
    a pair of curved torso tubes attached proximate to outer edges of a bottom surface of the torso pad, defining an interior region of the torso pad; and
    a torso support tube configured to bisect the interior region.

8. The traction device of claim 7, wherein the torso pad frame is slidably attached to the sliding spine assembly, such that the torso pad is configured to glide along a length of the sliding spine assembly.

9. The traction device of claim 7, wherein the torso pad frame is non-slidably attached to the sliding spine assembly, such that the torso pad is configured to remain stationary while the traction device is in use.

10. The traction device of claim 6, further comprising:
    a pair of handle brackets attached to the torso pad, each handle bracket comprising a handle extending outwardly therefrom.

11. A spinal decompression assembly, comprising:
    a sliding assembly;
    a belt attached to the sliding assembly, the belt configured to encircle a user in alignment with the user's spine;
    an adjustable length, pivotable vector bar extending outwardly from the sliding spine assembly and rotatably attached to the sliding assembly;
    an articulating joint located on a first end of the adjustable length, pivotable vector bar configured to engage with an articulating joint base attached to the sliding spine assembly to rotate the adjustable length, pivotable vector bar about more than one axis of rotation; and
    a strap assembly attached to the belt and a second end of the adjustable length, pivotable vector bar distal from the first end and to the belt, wherein when the user is positioned on the sliding assembly, moving the adjustable length, pivotable vector bar and the strap assembly in more than one axis of rotation applies traction to a user's spine.

12. The spinal decompression assembly of claim 11, further comprising:
   a head rest pad attached to a first end of the sliding spine assembly;
   a hip pad attached to a second end of the sliding spine assembly; and
   a torso pad positioned between the head rest pad and the hip pad.

13. The spinal decompression assembly of claim 11, further comprising:
   a leg press tube;
   a hollow split tube in the adjustable length, pivotable vector bar configured to accept and engage with the leg press tube; and
   a lock configured to lock the leg press tube.

14. The spinal decompression assembly of claim 11, wherein the adjustable length, pivotable vector bar comprises a hollow split rectangular tube configured to accept and engage with a leg press tube, wherein the leg press tube is locked in a desired position using a lock.

15. A method for using a traction device, comprising:
   positioning a user on the traction device;
   securing a belt around the user's waist;
   attaching a strap assembly to the belt and to a foot rest;
   pushing on the foot rest;
   rotating an adjustable length, pivotable vector bar assembly about more than one axis of rotation from a midline of the user's body, in response to pushing on the foot rest, wherein the adjustable length, pivotable vector bar assembly extends outwardly from a sliding spine assembly via an articulating joint located on the adjustable length, pivotable vector bar configured to engage with an articulating joint base attached to the sliding spine assembly; and
   applying traction to the belt with the strap assembly.

16. The method of claim 15, further comprising:
   aligning the strap assembly with the user's lumbar spine.

17. The method of claim 15, wherein positioning the user on the traction device further comprises:
   placing the user's torso on a torso pad; and
   positioning the user's feet against foot rests.

18. The method of claim 17, further comprising:
   varying the applied traction by sliding the torso pad along the sliding spine assembly.

19. The method of claim 17, wherein applying traction to the belt with the strap assembly further comprises:
   extending the user's legs;
   pressing on the foot rests with the user's legs; and
   applying traction from the strap assembly to the belt by pressing on the foot rests.

20. The method of claim 15, further comprising:
   measuring a force applied by the traction device to the user.

* * * * *